United States Patent [19]

Eggleton et al.

[11] 4,035,839
[45] July 12, 1977

[54] ULTRASONIC IMAGING

[75] Inventors: Reginald C. Eggleton; Francis J. Fry, both of Indianapolis, Ind.

[73] Assignee: Indianapolis Center For Advanced Research, Inc., Indianapolis, Ind.

[21] Appl. No.: 647,419

[22] Filed: Jan. 8, 1976

[51] Int. Cl.² .......................................... H04N 5/30
[52] U.S. Cl. .............................. 358/112; 73/67.5 R
[58] Field of Search ............... 178/6, 6.8, DIG. 18; 73/67.5 R, 67.5 H; 358/112

[56] References Cited
U.S. PATENT DOCUMENTS

| | | | |
|---|---|---|---|
| 3,282,087 | 11/1966 | Dickinson | 73/67.5 R |
| 3,475,551 | 10/1969 | Green et al. | 178/DIG. 18 |
| 3,559,465 | 2/1971 | Preston, Jr. | 73/67.5 H |
| 3,690,155 | 9/1972 | Eichler | 73/67.5 R |
| 3,715,482 | 2/1973 | Haines et al. | 73/67.5 H |

*Primary Examiner*—Richard Murray
*Attorney, Agent, or Firm*—Woodard, Weikart, Emhardt & Naughton

[57] ABSTRACT

Ultrasonic transmission imaging apparatus utilizing a pair of focused, large aperture transducers colinearly aligned and facing one another on opposite sides of a target. The receiving transducer and transmitting transducer are positioned to have a common focal point within the target. The transmitting transducer is energized by a continuous noncoherent noise source, and ultrasonic images are formed from the intensity modulation of the transmitted ultrasound at the receiving transducer.

9 Claims, 2 Drawing Figures

ULTRASONIC IMAGING

BACKGROUND OF THE INVENTION

1. Field of the Invention:

The invention is in the field of ultrasonic imaging.

2. Description of the Prior Art.

Ultrasonic transmission imaging and ultrasonic reflection imaging have been utilized for visualization of the interior of biological specimens in the prior art. The primary use has been made of ultrasonic reflection imaging, which inherently provides focused transmission and reception when a focused transducer is utilized.

It has been reported that ultrasonic transmission images possess several advantages over ultrasonic reflection images. Although earlier transmission imaging showed encouraging results, transmission imaging was soon replaced by reflection imaging because of the technological difficulties of transmission imaging and because of problems associated with the passage of ultrasonic energy through the entire body of a subject. However, with the advent of the technology, transmission ultrasonography is currently being reinvestigated and several such systems have been reported.

So far as applicants are aware, transmission ultrasonography has not been utilized employing focused transmitting and receiving transducers. In addition, so far as applicants are aware, neither ultrasonic transmission imaging nor reflection imaging has utilized random frequency noncoherent ultrasound of the imaging.

SUMMARY OF THE INVENTION

One embodiment of the present invention is an ultrasonic imaging apparatus comprising ultrasonic transducer means for transmitting a beam of ultrasonic energy toward a target and for receiving a portion of said energy after it has impinged upon said target, source means for energizing the ultrasonic transducer means to emit random frequency noncoherent ultrasound, and display means for displaying the relative intensities of ultrasound received by the ultrasonic transducer means.

It is an object of the present invention to provide ultrasonic imaging utilizing random frequency noncoherent ultrasound to produce superior images through the elimination of interference fringes around the structure being imaged.

It is a further object of the present invention to provide a focused ultrasonic transmission imaging system.

It is a still further object of the present invention to provide such a transmission imaging system which further includes the use of random frequency noncoherent ultrasound.

Further objects and advantages of the present invention shall be apparent from the following detailed description and accompanying figures.

DESCRIPTION OF THE PREFERRED EMBODIMENT

Figure 1:
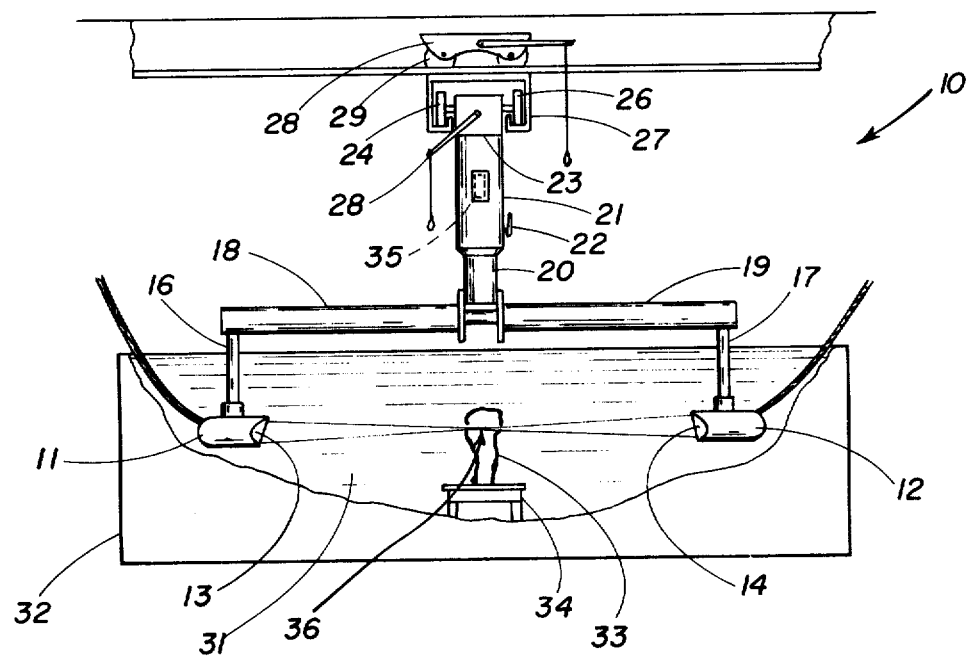
FIG. 1 is a side view of a transmission imaging apparatus and target specimen according to the present invention.

For the purposes of promoting an understanding of the principles of the invention, reference will now be made to the embodiment illustrated in the drawing and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring in particular to FIG. 1, there is shown an ultrasonic transmission imaging apparatus 10 according to the present invention. Apparatus 10 includes a transmitting transducer housing 11 and receiving transducer housing 12 including a transmitting transducer 13 and a receiving transducer 14, respectively. Transducer housing 11 is attached through vertical support pipe 16 and adjustable-length horizontal bar 18 to vertical shaft 20. Similarly, receiving transducer housing 12 is coupled by vertical support 17 and adjustable bar 19 to vertical shaft 20.

Shaft 20 is received within tube 21, and is operable to be moved in a vertical direction relative to tube 21 through the operation of, for example, hand control 22. Preferably, shaft 20 and its rigidly attached transducer housings 11 and 12 are moved in a vertical direction by motor means contained within housing 21.

Housing 21 is attached to a support block 23, which is movable along guide track 27 and includes rotatably attached rollers 24 and 26 to facilitate the movement of block 23 along track 27. A hand control 28 is provided for moving block 23 along track 27, but preferably this motion is also imparted by motor means contained within housing 21 operable to drive rollers 24 and 26. The motor means is indicated generally at 35, which is a motor and positioning assembly for providing a swept scan of target 33 and generating a signal indicative of the position of the ultrasound beam relative to the target.

Track 27 is fixed to a further support block 28, which is operable to be moved in a lateral direction along a track while being supported upon rollers such as 29. Apparatus of this general type is known in the art for providing a sweep scan of a targe specimen, for example in computer-assisted X-ray scanning operations.

In the ultrasonic apparatus 10 of FIG. 1, transducers 13 and 14 and their associated housings are received within a fluid 31 such as water which is contained in a tank assembly 32. A target specimen, which may be any biological specimen or human subject, etc. 33 is positioned within fluid 31 in tank 32 and supported for viewing on a platform 34.

Transducers 13 and 14 are large aperture, high sensitivity ceramic focused transducers. Preferably the angle of convergence of these transducers is greater than 20°. Transducers 13 and 14 are matched transducers and are positioned apart from one another such that they have a common focus point. This may be obtained by adjusting the length of adjustable support bars 18 and 19. Transducers 13 and 14 are low Q, wide band width, large aperture transducers. The plane of the focal point established by the adjustment of transducers 13 and 14 relative to one another, as indicated at 36, is then located at the appropriate depth in specimen 33 by moving housing 28 to the appropriate lateral position and then locking the apparatus in place.

Preferably, motor means mounted within housing 21 is energized to move support block 23 on its rollers 24 fore and aft as viewed in FIG. 1 to scan out a line through target 33. As the lines are scanned, the motor also raises and lowers the transducers by raising and lowering tube 20 to produce a complete swept scan of target 33 for the emphasized focal plane selected.

Figure 2:
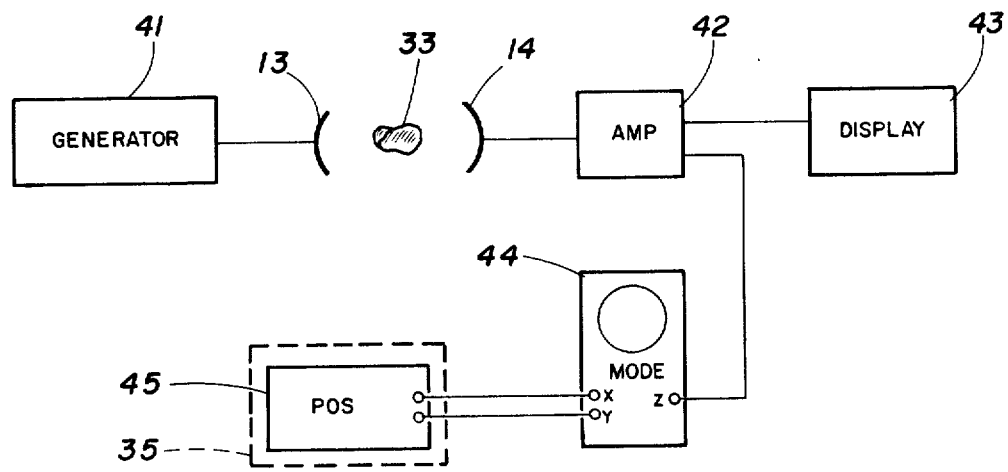
FIG. 2 is a block diagram representation of the system employed in FIG. 1.

Referring now to FIG. 2, there is shown a block diagram representation of the transducer imaging apparatus of FIG. 1 with added elements for energizing and receiving signals from the ultrasonic transducers. A random frequency noncoherent signal generator 41 supplies random frequency electrical signals to transmitting transducer 13 which emits random frequency noncoherent ultrasound to the emphasized focal plane within target 33. Receiving transducer 14, positioned to receive the ultrasonic energy from the same focal plane receives the energy as modified by target 33 and couples this output to amplifier 42. The output of amplifier 42 is an indication of the instantaneous intensity of received ultrasound at a given point in the sweep across target 33 and may be coupled to various types of displays such as 43. One type of display which may be used is an oscilloscope 44, receiving its Z (intensity) signal from amplifier 42. The X and Y beam positions for oscilloscope 44 are obtained from position-sensing means 45 included within motor and positioning assembly 35 (FIG. 1). Such position indicators are well known in the art of ultrasonic imaging and need not be discussed further herein.

Random frequency noncoherent ultrasound may also be utilized in reflection imaging, and the apparatus of FIGS. 1 and 2 would need only be modified to, for example, utilize transducer 14 as both a receiving and transmitting transducer with connections to both amplifier 42 and generator 41. Transducer 13 and its associated mechanical parts could be eliminated from the apparatus. Thus, ultrasonic transducer means for transmitting beam of ultrasonic energy toward a target and for receiving a portion of said energy after it has impinged upon the target may be provided by either a single transducer or a pair of transducers, as described above.

While the quality of prior art ultrasonic images obtained using a continuous coherent wave source is usually degraded due to constructive and destructive interferences, these undesirable interferences are obviated by using a continuous noncoherent noise source. Ultrasonic transmission images obtained using a continuous noise source are generally superior to those obtained using a continuous coherent wave source. Utilized as described above in conjunction with random frequency ultrasound, focused transmission imaging provides further improvements in images obtained through the emphasis of a particular focal plane as the transducers are swept over the target being imaged. A desired plane to be viewed can be selected with the apparatus as described above, and the image at this plane is emphasized similar to the result obtained with reflection imaging.

While there have been described above the principles of this invention in connection with specific apparatus, it is to be clearly understood that this description is made only by way of example and not as a limitation in the scope of the invention.

What is claimed is:
1. Ultrasonic imaging apparatus comprising:
   ultrasonic transducer means for transmitting a beam of ultrasonic energy toward a target and for receiving a portion of said energy after it has impinged upon said target;
   scan means for producing relative motion between the ultrasonic transducer means and the target;
   source means for energizing the ultrasonic transducer means to emit random frequency non-coherent ultrasound; and
   display means for displaying at positions corresponding to the relative motion produced by said scan means the relative intensities of a wide bandwidth of ultrasound received by the ultrasonic transducer means.

2. The apparatus of claim 1 in which the ultrasonic transducer means comprises a transmitting transducer and a receiving transducer operable to be positioned facing one another on opposite sides of the target.

3. The apparatus of claim 1 in which said scan means additionally includes means for producing relative motion between the ultrasonic transducer means and the target such that a determinable path of impingement of said beam on the target is produced.

4. The apparatus of claim 3 in which the display means includes sweep means for displaying the relative intensities of received ultrasound over said determinable path.

5. The apparatus of claim 4 in which the ultrasonic transducer means comprises a transmitting transducer and a receiving transducer operable to be positioned facing one another on opposite sides of the target.

6. Ultrasonic transmission imaging apparatus comprising:
   a transmitting ultrasonic transducer having a first focal length;
   source means for energizing the transmitting transducer to emit ultrasound;
   a receiving transducer, having a second focal length, positioned to receive the ultrasound from the transmitting transducer, the distance between said transducers being essentially the sum of the first focal length and the second focal length; and
   display means for displaying the intensity of the ultrasound received by the receiving transducer.

7. The apparatus of claim 6 which further comprises scan means for producing relative motion between the ultrasonic transducer means and the target such that a determinable path of impingement of said beam on the target is produced.

8. The apparatus of claim 7 in which the display means includes sweep means for displaying the relative intensities of received ultrasound over said determinable path.

9. The apparatus of claim 6 in which the source means energizes the transmitting transducer to emit random frequency noncoherent ultrasound.

* * * * *